United States Patent [19]

Lee et al.

[11] 4,236,014

[45] Nov. 25, 1980

[54] PRODUCTION OF THE AMMONIUM SALT OF 3,5-DINITRO-1,2,4-TRIAZOLE BY SOLVENT EXTRACTION

[75] Inventors: Kien Y. Lee; Donald G. Ott, Los Alamos, N. Mex.

[73] Assignee: The United States of America as represented by the United States Department of Energy, Washington, D.C.

[21] Appl. No.: 92,155

[22] Filed: Nov. 7, 1979

[51] Int. Cl.$^3$ ............................................. C07D 249/14
[52] U.S. Cl. ....................................................... 548/267
[58] Field of Search .......................................... 548/267

[56] References Cited

U.S. PATENT DOCUMENTS

| | | | |
|---|---|---|---|
| 2,987,520 | 6/1961 | Sickman | 548/267 |
| 3,054,800 | 9/1962 | Burchfield et al. | 548/267 |
| 3,111,524 | 11/1963 | Wiley et al. | 548/267 |
| 3,165,753 | 1/1965 | Smith et al. | 548/267 |

FOREIGN PATENT DOCUMENTS 210174  6/1968  U.S.S.R. ................................ 548/267

OTHER PUBLICATIONS

Mattila et al, Ind. Eng. Chem., Process Des. Dev., vol. 16, pp. 469-472.

Singh et al, J. Radioanal. Chem., vol. 36, pp. 331-336, (1977).

Bagal et al, Khim. Geterotsiklicheskikh Soedinenii, vol. 6, pp. 259-264, 558-562, (1970).

*Primary Examiner*—Alton D. Rollins
*Attorney, Agent, or Firm*—James E. Denny; Paul D. Gaetjens; Edward C. Walterscheid

[57] ABSTRACT

The ammonium salt of 3,5-dinitro-1,2,4-triazole has utility as a chemical explosive. In accordance with the present invention, it may readily be produced by solvent extraction using high-molecular weight, water-insoluble amines followed by amination with anhydrous ammonia gas. The aqueous reaction mixture produced in the synthesis of the parent compound, 3,5-dinitro-1,2,4-triazole, is quite suitable--and indeed is preferred---for use as the feed material in the process of the invention.

6 Claims, 1 Drawing Figure

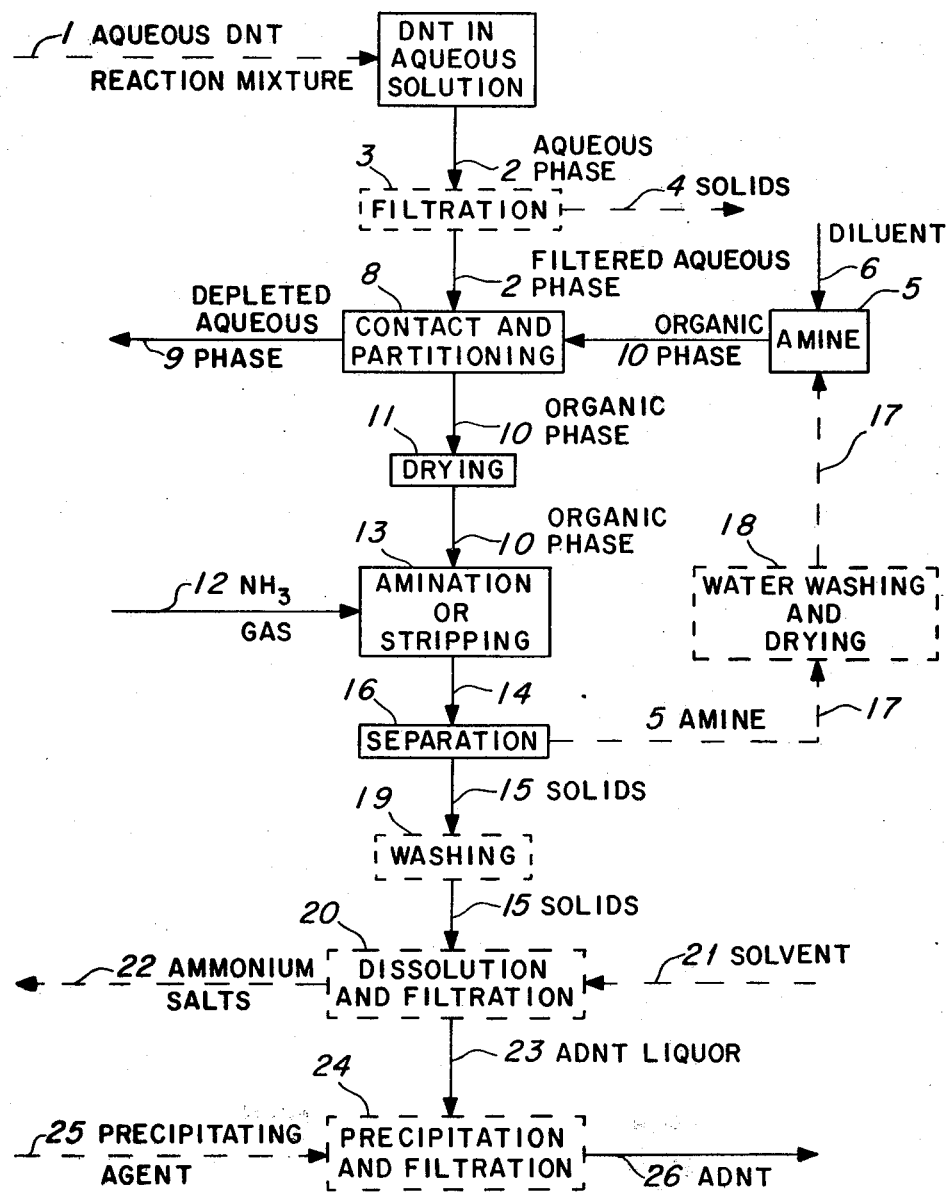
Fig.

PRODUCTION OF THE AMMONIUM SALT OF 3,5-DINITRO-1,2,4-TRIAZOLE BY SOLVENT EXTRACTION

BACKGROUND OF THE INVENTION

1. Field of the Invention

The invention described herein relates to a method for preparing the ammonium salt of 3,5-dinitro-1,2,4-triazole and more particularly to a method of preparing the ammonium salt of 3,5-dinitro-1,2,4-triazole by solvent extraction using high-molecular-weight, water-insoluble amines. It is a result of contract W-7405-ENG-36 with the Department of Energy.

The ammonium salt of 3,5-dinitro-1,2,4-triazole (ADNT) is an explosive with several interesting properties. It is quite soluble in water (28 g/100 ml), has a calculated $P_{CJ}$ of 262 kbars at its crystal density of 1.632 g/cm$^3$, melts with loss of ammonia at 170° C., has ERL Type 12/12B drop-weight impact sensitivities of 59/80 cm, and has a Henkin critical temperature of 222° C.

2. Description of the Prior Art

Several techniques for the preparation of the parent compound, 3,5-dinitro-1,2,4-triazole (DNT), have been reported in the literature, but the preferred method has been synthesis from 3,5-diamino-1,2,4-triazole (guanazole, DAT), sulfuric acid, and excess sodium nitrite. The overall reaction proceeds as:

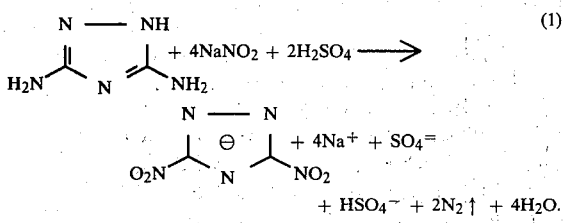

The ammonium salt, i.e., ADNT, has been prepared in the past by amination of DNT in anhydrous ether after continuous extraction from its reaction mixture by the ether. Unfortunately, the ether extraction is hazardous, time-consuming, and inefficient.

Liquid, high-molecular-weight, water-insoluble amines which act as anion exchangers are known to be useful extractants for removal of certain acidic constituents and anionic complexes of various metals from aqueous solution. The literature indicates that hydrometallurgical separations, waste-water treatment, and recovery of valuable acids can be achieved using agents of this type. Insofar as can be ascertained, however, there is nothing in the literature which suggests a procedure in which a liquid anion exchanger is used to extract an organic acid from its aqueous medium and in which the organic acid is recovered as its ammonium salt by amination of an amine salt in the organic phase with anhydrous ammonia.

OBJECTS OF THE INVENTION

An object of the invention is to provide a less hazardous method for production of ADNT.

Another object is to provide a more efficient process for the production of ADNT.

Yet another object is to provide a more rapid method for the production of ADNT.

Other objects, advantages, and novel features of the invention will become apparent to those skilled in the art upon examination of the following detailed description of a preferred embodiment of the invention and the accompanying drawing.

SUMMARY OF THE INVENTION

The invention is directed to a method for preparing the ammonium salt of 3,5-dinitro-1,2,4-triazole by solvent extraction using high-molecular weight, water-insoluble amines. In its broad aspect, the invention encompasses a method for preparing the ammonium salt of 3,5-dinitro-1,2,4-triazole having the following steps. An aqueous phase and an organic phase are formed, with the aqueous phase comprising an aqueous solution of 3,5-dinitro-1,2,4-triazole and the organic phase comprising a desired ratio of a water-insoluble secondary or tertiary aliphatic amine capable of acting as an anion exchanger and a desired diluent. The diluent should have a good solubility for ammonia gas and little or no solubility for the ammonium salt of 3,5-dinitro-1,2,4-triazole. The aqueous phase is contacted with the organic phase for a time sufficient for partitioning of the 3,5-dinitro-1,2,4-triazole between the two phases to occur, and the depleted aqueous phase is then separated from the organic phase. After the organic phase is dried to remove residual water, it is contacted with ammonia gas, and the precipitate produced by the reaction of the ammonia gas with the amine salt of the 3,5-dinitro-1,2,4-triazole is removed from the organic phase.

This method is advantageous in that it avoids the use of ether extraction and is therefore much less hazardous than the prior art techniques for the production of this salt of 3,5-dinitro-1,2,4-triazole. Moreover, it provides for more rapid and efficient preparation of the ammonium salt than is possible using the techniques taught in the literature. It is readily scalable to quantity production and readily permits the use of the reaction mixture formed in the synthesis of 3,5-dinitro-1,2,4-triazole in accordance with reaction (1) as the feed material.

BRIEF DESCRIPTION OF THE DRAWING

The FIGURE is a flow chart of the process of the invention.

DESCRIPTION OF THE INVENTION

As shown by the FIGURE, production of ADNT in accordance with the process of the invention is predicated on the extraction of DNT from its aqueous solution by an appropriate secondary or tertiary aliphatic amine followed by reaction of the resultant amine salt with ammonia gas to form the ADNT. The DNT may readily be extracted directly from the aqueous reaction mixture in which it is prepared. The extraction by the aliphatic amine is achieved by the ion-pair formation of the amine salt in organic diluent between the base extractant and the acidic DNT ($pK_a = -0.66$) aqueous solution as shown by the following reaction:

$$(R_3N)_{org} + (DNT^- + H^+)_{aq} \rightleftharpoons (R_3NH^+DNT^-)_{org} \quad (2)$$

where $R_3N$ is the aliphatic amine and the subscripts "org" and "aq" indicate the organic and aqueous phases respectively. If one of the R groups is hydrogen, the aliphatic amine is a secondary amine, otherwise it is a tertiary amine. The R groups may be straight or branched chain alkyls. In the practice of the invention, any secondary or tertiary amine may be used which is a water-insoluble liquid anion exchanger.

The formation of ADNT as an insoluble solid in the organic phase is completed by reaction of the amine salt with the basic stripping agent, i.e., ammonia gas, which regenerates the amine to its free base form:

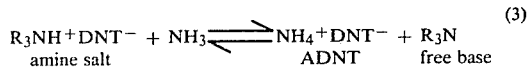

$$R_3NH^+DNT^- + NH_3 \rightleftharpoons \underset{ADNT}{NH_4^+DNT^-} + \underset{free\ base}{R_3N} \qquad (3)$$

amine salt

As indicated on the flow sheet of the FIGURE, the amine in its free base form may readily be recycled for re-use in the extraction of DNT from the aqueous reaction mixture.

Generally, it has been found that the extraction efficiency is improved if the aliphatic amine is diluted with a suitable organic solvent or diluent. Preferred solvents give a good and reasonably rapid separation between the organic and aqueous phases, have a high solubility for ammonia gas, and have little or no solubility for ADNT. Aromatic solvents are generally preferred over aliphatic solvents in that the solubility of amine salts is greater in them. Toluene has been found to provide excellent results and is the preferred diluent.

In the flow chart of the FIGURE, steps which are critical to the practice of the invention are shown by solid lines, whereas those which are merely preferred are indicated by the dashed lines. As shown, the process of the invention commences with formation of an aqueous phase 2 which is an aqueous solution of DNT. As a practical matter, it is preferred that aqueous phase 2 is the aqueous DNT reaction mixture 1 obtained in the synthesis of DNT in accordance with reaction (1). If reaction mixture 1 is used, aqueous phase 2 preferably had decolorizing carbon added and then undergoes filtration 3. If desired, the concentration of DNT in filtered aqueous phase 2 can be determined spectrophotometrically based on the DNT absorption at 285 nm.

A suitable secondary or tertiary water-insoluble amine 5 is then mixed with a desired diluent or solvent 6 in a desired ratio and the resultant organic phase 10 contacted 8 with aqueous phase 2 for a time sufficient for the DNT to be partitioned to the organic phase 10. On a bench scale, this is readily accomplished by mixing aqueous phase 2 and organic phase 10 in a desired ratio in a separatory funnel, shaking the mixture vigorously until equilibrium occurs, and then allowing the mixture to stand for a time sufficient for the depleted aqueous phase 9 to separate from the organic phase 10. Organic phase 10 is then removed from contact with depleted aqueous phase 9 and passed through a drying step 11 to remove any residual water. The drying is easily accomplished with anhydrous magnesium sulfate which is then filtered from organic phase 10.

Ammonia gas 12 is then contacted with organic phase 10 in the amination or stripping step 13 until no further solid precipitates from organic phase 10. The necessary contact is readily achieved by bubbling gas 12 through organic phase 10 at a desired flow rate. It is highly preferable that the organic phase 10 be cooled substantially below room temperature before amination occurs. Cooling to the range of 0°–4° C. is readily accomplished by means of an ice bath. When there is no further reaction, mixture 14 of solids 15 and amine 5 is subjected to separation step 16 wherein the solids 15 and amine 5 are separated. This is readily accomplished by filtration. The amine 5 (and its accompanying diluent 6) is then preferably recycled 17 through water washing and drying step 18 to be used once again in contact and partitioning step 8. If aqueous phase 3 contained only DNT, essentially all of solids 15 is ADNT. If, however, reaction mixture 1 is used, the bulk of solids 15 will be ADNT.

In the preferred embodiment using reaction mixture 1, the solids 15 are then washed several times with an appropriate solvent to remove any amine still adhering to them. Toluene is quite suitable for this purpose. To separate ADNT from any other ammonium salts 22 which may be present, solids 15 pass through dissolution and filtration step 20. In step 20, the solids 15 are stirred into solvent 21 at room temperature for a time sufficient to ensure complete dissolution of the ADNT. Solvent 21 is selected from the class in which ADNT is soluble but other ammonium salts are not. Acetonitrile and ethyl acetate are both suitable for use as solvent 21 but ethyl acetate is preferred. A mixture of 3 grams of solids 15 per 100 ml of ethyl acetate is quite adequate to assure that the ADNT will be fully dissolved. Dissolution of the ADNT in step 20 may be accelerated by adding a small amount of acetone to solvent 21. Any other ammonium salts 22 which may be present remain as solids and are removed from the resultant ADNT liquor 23 by filtration.

The ADNT is then crystallized from liquor 23. This may be accomplished by evaporation of solvent 21 but preferably occurs through addition of a precipitation agent 25 to liquor 23. Toluene has been found to be an excellent precipitation agent 25. The pure crystalline ADNT 26 is readily separated from liquor 23 by filtration, 24.

The Table shows the effect of amine concentration and type of amine in various solvents on the percentage of extraction and yield of ADNT produced in accordance with the process of the invention. As used in the Table, Alamine 304 and Alamine 336 are tradenames for tertiary aliphatic amines produced by General Mills Chemicals, Inc. Alamine 304 is trilauryl amine and is a viscous liquid with a density of 0.82 g/cc. In Alamine 336 the alkyl groups are a $C_8$–$C_{10}$ mixture. Amberlite LA-2 is a tradename for a secondary amine produced by Rohm & Haas Co. which has a molecular weight in the range of 353–395. In Amberlite LA-2, one of the organic groups is lauryl and the other is a branched alkyl of about 13 carbons. The abbreviations DCM and DCE refer to dichloromethane and dichloroethane, respectively.

For the runs set forth in the Table, reaction (1) was carried out on a 0.3-mole scale (excess sodium nitrite). Assuming theoretical yield, the reaction mixture 1 used in each run contained:

0.3 mole NaDNT, 1.15 moles $Na_2SO_4$, 0.3 mole $NaHSO_4$, 0.05 mole $H_2SO_4$, with the remainder being water. The total solution volume ranged from 1.78 to 1.85 liters in the different runs.

TABLE

| Amine | Solvent | Amine/DNT Mole Ratio | Extraction Efficiency (%) | ADNT Recovered (%) |
|---|---|---|---|---|
| Alamine 304 | Toluene | 0.4 | 52 | 87 |
| " | " | 0.8 | 76 | 92 |
| " | " | 1.0 | 83 | 89 |
| " | " | 1.4 | 92 | 86 |
| " | " | 2.0 | 98 | 80 |
| " | DCM | 1.0 | 85 | 78 |
| " | DCE | 1.0 | 84 | 77 |
| Amberlite LA-2 | Toluene | 1.0 | 77 | 78 |
| " | DCE | 1.0 | 78 | 75 |

TABLE-continued

| Amine | Solvent | Amine/DNT Mole Ratio | Extraction Efficiency (%) | ADNT Recovered (%) |
|---|---|---|---|---|
| Alamine 336 | Toluene | 1.0 | 84 | 85 |

In these runs, in amination step 13 the organic phase 10 was cooled in an ice bath and anhydrous ammonia gas 12 bubbled through the cooled organic phase 10 at a flow rate of 20–30 cc/min until the amination was completed. Typically, this took about one hour with 0.2 mole of DNT-amine salt in organic phase 10.

For the amines used in the runs set forth in the Table, the extraction efficiency for DNT is proportional to the amount of the extractant used. The extraction efficiency in percent is given by $$\frac{C - C_w}{C} \times 100$$

where $C$ is the total initial DNT mole concentration in the aqueous phase and $C_w$ is the mole concentration of DNT found in the equilibrium aqueous phase, i.e., the aqueous phase after there has been sufficient contact between the organic and aqueous phases for partitioning of the DNT to be completed. As evidenced by the data of the Table, the higher the amine/DNT mole ratio, the higher is the extraction efficiency obtained.

As set forth in the Table, the percentage of ADNT recovered is based on the amount of DNT calculated in the aqueous phase after extraction. Contrary to the extraction efficiency, the ADNT yield appears to be independent of the amine/DNT mole ratio for these runs. As evidenced by the data of the Table, the recovery of DNT as ADNT is highest at a 0.8:1 amine/DNT mole ratio. Although there is a relatively low extraction efficiency at this ratio, this may readily be compensated for by repeating the extraction of the depleted aqueous phase. By so doing, an extraction efficiency in excess of 90% can be obtained.

Although the foregoing description has been limited to the production of ADNT, it will be apparent that the process of the invention is applicable to the production of the ammonium salts of a wide variety of organic compounds which are acidic in aqueous solution.

The foregoing description of a preferred embodiment of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. A method for the production of the ammonium salt of 3,5-dinitro-1,2,4-triazole which comprises:

(a) forming an aqueous phase which comprises an aqueous solution of 3,5-dinitro-1,2,4-triazole;
   (b) forming an organic phase which comprises in a desired ratio a water-insoluble secondary or tertiary aliphatic amine capable of acting as an anion exchanger and a desired diluent, said diluent having a good solubility for ammonia gas and little or no solubility for the ammonium salt of 3,5-dinitro-1,2,4-triazole;
   (c) contacting said aqueous phase with said organic phase for a time sufficient for partitioning of said 3,5-dinitro-1,2,4-triazole between said aqueous phase and said organic phase to occur;
   (d) separating the depleted aqueous phase from said organic phase;
   (e) drying said organic phase;
   (f) contacting said dried organic phase with ammonia gas; and
   (g) separating the precipitate produced by the reaction of said ammonia gas with the amine salt of said 3,5-dinitro-1,2,4-triazole from said organic phase.

2. The method of claim 1 wherein said aqueous phase comprises a reaction mixture formed in accordance with the following reaction

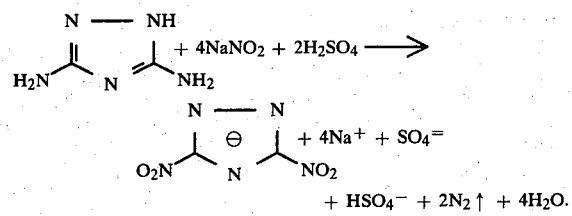

and wherein the method comprises the additional steps of (h) washing said precipitate with a solvent in which said amine is soluble but said precipitate is insoluble;
   (i) dissolving said precipitate in a solvent in which other ammonium salts formed when said organic phase is contacted with said ammonia gas are insoluble;
   (j) removing any solids from the resultant solution;
   (k) precipitating the ammonium salt of 3,5-dinitro-1,2,4-triazole therefrom; and
   (l) removing said precipitated salt from said solution.

3. The method of claim 1 or claim 2 wherein said ammonia gas is anhydrous and is contacted with said organic phase in an amount and for a time sufficient for essentially all the amine salt of said 3,5-dinitro-1,2,4-triazole in said organic phase to react with said ammonia gas.

4. The method of claim 3 wherein said organic phase is cooled substantially below room temperature before being contacted with said ammonia gas.

5. The method of claim 4 wherein said diluent is toluene.

6. The method of claim 5 wherein said amine is trilauryl amine.

* * * * *

UNITED STATES PATENT OFFICE
CERTIFICATE OF CORRECTION

Patent No. 4,236,014            Dated November 25, 1980

Inventor(s) Kien Y. Lee and Donald G. Ott

It is certified that error appears in the above-identified patent and that said Letters Patent are hereby corrected as shown below:

The name of inventor has been misspelled. The name should read:

Kien-yin Lee

Signed and Sealed this

Thirty-first Day of March 1981

[SEAL]

*Attest:*

RENE D. TEGTMEYER

*Attesting Officer*      *Acting Commissioner of Patents and Trademarks*